(12) United States Patent
Ziehe et al.

(10) Patent No.: US 10,654,765 B2
(45) Date of Patent: May 19, 2020

(54) METHOD FOR PRODUCING A LATENT HEAT STORAGE MATERIAL AND DIALKYL ETHER AS A LATENT HEAT STORAGE MATERIAL

(71) Applicant: Sasol Germany GmbH, Hamburg (DE)

(72) Inventors: Holger Ziehe, Itzehoe (DE); Achim Weitze, Brunsbuttel (DE); Thoralf Gross, Brunsbuttel (DE)

(73) Assignee: Sasol Germany GmbH, Hamburg (DE)

( * ) Notice: Subject to any disclaimer, the term of this patent is extended or adjusted under 35 U.S.C. 154(b) by 184 days.

(21) Appl. No.: 15/152,713

(22) Filed: May 12, 2016

(65) Prior Publication Data

US 2016/0257628 A1   Sep. 8, 2016

Related U.S. Application Data

(63) Continuation of application No. 12/863,643, filed as application No. PCT/DE2009/000036 on Jan. 15, 2009, now abandoned.

(30) Foreign Application Priority Data

Jan. 23, 2008   (DE) .................. 10 2008 005 721

(51) Int. Cl.
| | | |
|---|---|---|
| C07C 1/24 | (2006.01) | |
| C07C 5/03 | (2006.01) | |
| C09K 5/06 | (2006.01) | |
| C07C 41/09 | (2006.01) | |
| C07C 43/04 | (2006.01) | |

(Continued)

(52) U.S. Cl.
CPC .................. *C07C 1/24* (2013.01); *C07C 5/03* (2013.01); *C07C 9/22* (2013.01); *C07C 29/80* (2013.01); *C07C 41/09* (2013.01); *C07C 43/04* (2013.01); *C09K 5/063* (2013.01); *C07C 2523/755* (2013.01)

(58) Field of Classification Search
None
See application file for complete search history.

(56) References Cited

U.S. PATENT DOCUMENTS

| | | | | |
|---|---|---|---|---|
| 2,587,753 A | * | 3/1952 | O'Connor | ............... C07C 29/74 558/291 |
| 5,650,546 A | | 7/1997 | Chaudhari et al. | |
| 6,200,681 B1 | | 3/2001 | Jahns et al. | |

(Continued)

FOREIGN PATENT DOCUMENTS

| | | |
|---|---|---|
| DE | 19813562 | 11/1998 |
| DE | 102004056786 | 7/2005 |

(Continued)

OTHER PUBLICATIONS

Asinger, et al., Alkane und Cycloalkane Eugen Muller: Houben-Weyl's Methoden der Organischen Chemie, (only the formulas are relevant), 1970.

(Continued)

*Primary Examiner* — Philip Y Louie
(74) *Attorney, Agent, or Firm* — Bushman Werner, P.C.

(57) ABSTRACT

The invention relates to a method for producing latent heat storage material from linear alcohols by dehydrating to dialkyl ethers or to olefins, and hydrogenating to paraffins and dialkyl ether as a latent heat storage material.

14 Claims, 6 Drawing Sheets

Figure 1:
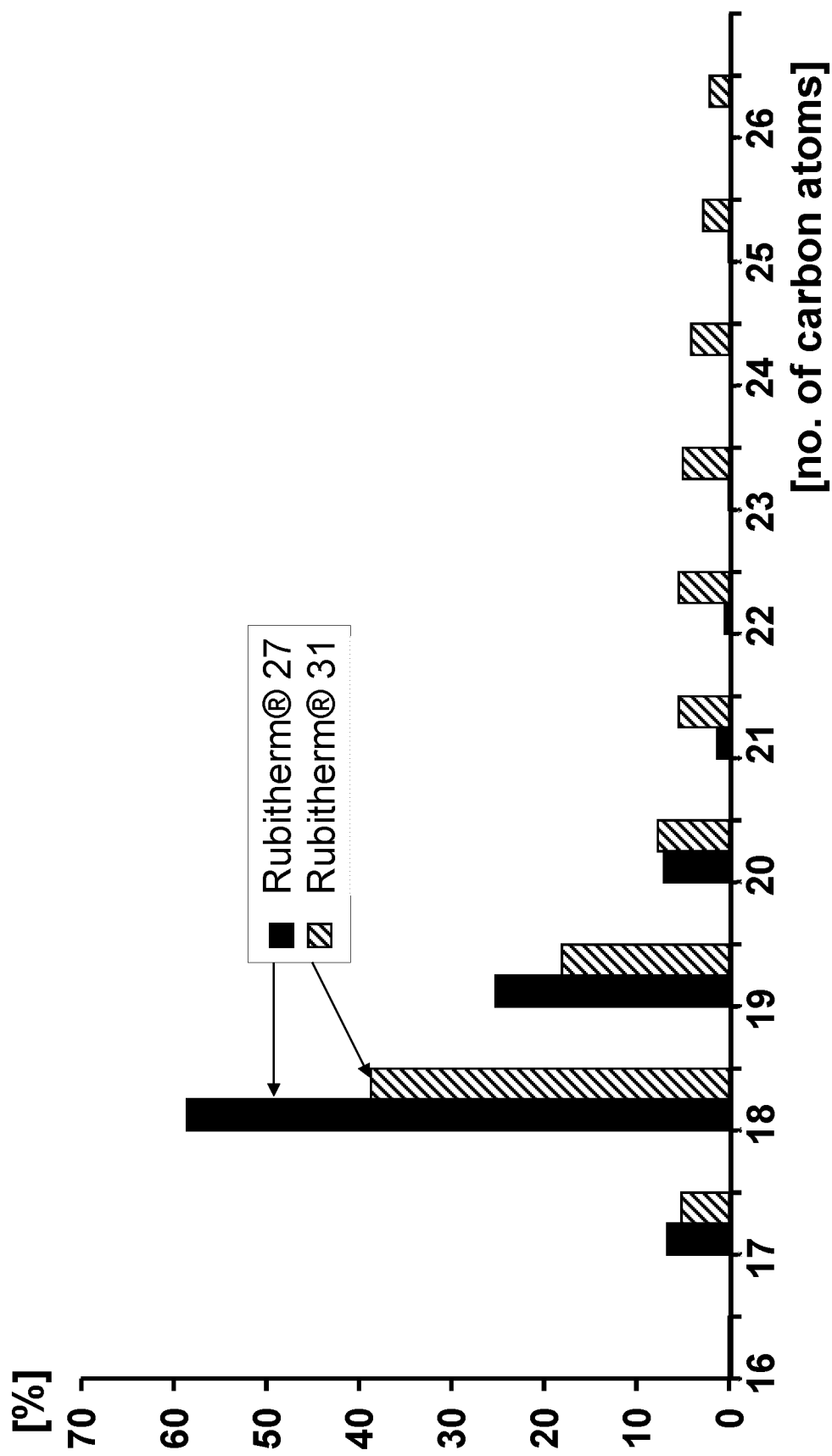

(51) Int. Cl.
*C07C 9/22* (2006.01)
*C07C 29/80* (2006.01)

(56) References Cited

U.S. PATENT DOCUMENTS

| | | | |
|---|---|---|---|
| 6,230,444 B1 * | 5/2001 | Pause | C09K 5/063 165/48.1 |
| 2006/0199011 A1 | 9/2006 | Jahns | |
| 2008/0008858 A1 * | 1/2008 | Hong | E04D 5/12 428/143 |
| 2008/0177121 A1 * | 7/2008 | Wu | C08F 10/00 585/530 |
| 2008/0287722 A1 | 11/2008 | Dierker | |
| 2008/0293977 A1 * | 11/2008 | Ziehe | C07C 29/54 568/877 |
| 2009/0169893 A1 | 7/2009 | Ikegami et al. | |

FOREIGN PATENT DOCUMENTS

| | | | |
|---|---|---|---|
| EP | 1950265 | 7/2008 | |
| WO | WO0138453 | 5/2001 | |
| WO | WO-2005123639 A1 * | 12/2005 | C07C 29/54 |
| WO | WO2007058003 | 5/2007 | |
| WO | WO2007107171 | 9/2007 | |

OTHER PUBLICATIONS

Sasol Olefins & Surfactants, "NACOL C6—C22 Single Fractions, NAFOL C10—C28 Blends, Linera Alcohols" company publication of Sasol Germany GmbH, Nov. 2003.
Sasol Olefins & Surfactants, NACOL Ether, company publication of Sasol Germany GmbH, May 2007.
Cho, Jeong-Sook et al.: "Microencapsulation of octadecane as a phase-change material by interfacial polymerization in an emulsion system," Colloid Polymer Sci, vol. 280, 2002.
Alvarado J. L. et al.: "Characterization of supercooling suppression of microencapsulated phase change material by using DCS" Journal of Thermal Analysis and Cal, vol. 86, 2006.
Bo, He et al.: "Tetradecane and hexadecane binary mixtures as phase change materials (PCMs) for cool storage in district cooling systems," Energy, vol. 24, 1999, pp. 1015-1028.
Babich, et al.: "The search for novel energy storage materials using differential scanning calorimetry", Thermochimica Acta 210, 1992, p. 83-88.
Himran, et al.: "Characterization of Alkanes and Paraffin Waxes for Application as Phase Change Energy Storage Medium" Energy Sources, vol. 10, 1994, p. 117-128.

* cited by examiner

METHOD FOR PRODUCING A LATENT HEAT STORAGE MATERIAL AND DIALKYL ETHER AS A LATENT HEAT STORAGE MATERIAL

CROSS REFERENCE TO RELATED APPLICATION

This application is a continuation of U.S. application Ser. No. 12/863,643 filed Oct. 4, 2010, which is a U.S. national application of PCT/DE2009/000036 filed Jan. 15, 2009, which claims priority to German Application DE102008005721.5, filed Jan. 23, 2008, the disclosures of which are all incorporated herein by reference for all purposes.

FIELD OF THE INVENTION

The invention relates to a method for producing a latent heat storage material from linear alcohols and dialkyl ether as a latent heat storage material.

BACKGROUND OF THE INVENTION

Phase change materials (PCMs) may release or absorb, respectively, or store, respectively, heat by melting or solidifying, respectively, within a defined temperature range, and thus function as latent heat storage materials. This principle of heat storage may also be used, for example, in the wall insulation of buildings. Such latent heat storage materials are, e.g. in the form of micro-capsules, introduced into the wall plaster or into gypsum plaster-boards and liquefy during the day with high heat input. The heat absorbed is stored in the wall and keeps the interior cool. Following cooling during the evening hours and at night, the liquid storages solidify and release the crystallization heat to the environment. In that, the interior is warmed up.

As latent heat storage materials, predominantly paraffins and paraffin mixtures are used. Commercially available paraffin mixtures for PCM applications are, for example, Rubitherm® 27 and Rubitherm® 31. The main component of the above Rubitherm® mixtures is $C_{18}$ paraffin with a content of only 59 or 39% by mass, respectively. These paraffin mixtures consist of even- and odd-numbered linear paraffins in the chain length range of $C_{17}$ to $C_{21}$ or $C_{17}$ to approx. $C_{30}$, respectively, however, have a portion of linear chains of 98.0 or 95.6% by mass, respectively.

Paraffins may also be produced by hydrogenation of commercially available alpha-olefins. These, however, only have linearities of approx. 90 to less than 95% by mass in the $C_{16}$ to $C_{18}$ range, and have the disadvantage that due to the branched side products, their melting enthalpy is clearly lower in comparison to that of highly linear paraffins.

It was found, that mixtures of even-numbered and odd-numbered paraffins, such with different chain lengths and/or higher branched portions have the disadvantage that these have wide or several different melting peaks, wherein, when these peaks are too far apart with regard to the temperature, normally only part of the possible melting enthalpy can actually be used.

SUMMARY OF THE INVENTION

The object of the present invention therefore is the provision of highly linear compounds, like paraffins, with a defined chain length for use as latent heat storage materials. Herewith, the following advantages are achieved: on the one hand, the melting range of highly pure paraffins is clearly narrower compared to paraffin mixtures, and thus the full storage capacity can be used at low temperature differences already. On the other hand, the melting enthalpy of the pure substance is clearly higher than that of the mixtures.

The invention is defined by the subject matter of the independent claims. Preferred embodiments are the subject matter of the dependent claims or described hereinafter.

DESCRIPTION OF PREFERRED EMBODIMENT

Pure substances, in particular linear paraffins with defined chain lengths, have higher melting heats and narrower melting ranges than branched paraffins or paraffin mixtures. Via the selection of the structure and chain length of the paraffin, the melting temperature of the PCM can be set across a wide temperature range.

The paraffins preferably fulfill the following specification independent from each other:
a) they have even-numbered chain lengths at more than 95% by mass, in particular more than 98% by mass,
b) they exclusively have a certain C-number at more than 95% by mass, in particular more than 97% by mass,
c) they are linear at more than 95% by mass.

The dialkyl ethers respectively have two residues R, so that the limit values are respectively lower. The dialkyl ethers preferably fulfill the following specification independent from each other:
a) they have even-numbered chain lengths at more than 91% by mass, in particular more than 95% by mass,
b) they exclusively have a certain C-number at more than 91% by mass, in particular more than 94% by mass, and
c) they are linear at more than 91% by mass, in particular more than 95% by mass.

In particular, the alcohols are purified or selected, respectively, such that they already fulfill the above limit values for the paraffins, for producing the dialkyl ethers as well as for producing the paraffins. The alcohols which are purified are preferably purified through distillation.

The latent heat storage material is obtainable by dehydrating linear fatty alcohols to dialkyl ethers or to olefins, wherein the latter are subsequently hydrogenated to paraffins. Fatty alcohols in terms of this invention are alcohols with C-numbers higher than or equal to 6 and preferably with terminal hydroxy groups. Particularly suitable starting materials in case of the paraffins are cetyl alcohol or stearyl alcohol, and in case of the dialkyl ethers lauryl alcohol or myristyl alcohol.

It was thus surprisingly found that particularly paraffins are suited as linear paraffins for PCM applications, which can be produced by dehydrating linear alcohols to linear olefins and their subsequent hydrogenation. The linear alcohols used are easily available as single sections and are preferably based on renewable vegetable or animal raw materials, in particular vegetable ones, like e.g. palm oil, palm kernel oil, coconut oil, rapeseed oil or other vegetable oils.

Alcohols obtainable from natural raw materials are characterized by an increased linearity of e.g. >98% by mass. The paraffins produced therefrom are therefore surprisingly well suited for application in PCMs. Beside native sources for the alcohols, ethylene oligomerisation according to the Ziegler synthesis, too, is a source for the alcohols used according to the invention.

Alternatively, paraffins may also be used, which can be produced by dehydrating synthetic alcohols. In the chain length range $C_{16}$ to $C_{18}$, however, normally these frequently only have linear ties from 93 to 99%.

The use of linear paraffins as PCMs is known, just like the production of paraffins from fatty alcohols. So far, however, no paraffins have been described for this application as latent heat storage material, which are produced from dehydrated alcohols, in particular such ones, which are available from renewable raw materials.

In the past, the skilled person always assumed that the production of alcohols from paraffins is a refinement step, in which the alcohol has a higher value than the paraffin. Now, it was not to be expected that the reverse path, i.e. the production of paraffin from an alcohol, is economically reasonable. However, it was now demonstrated that paraffins from alcohol dehydration result in particularly pure paraffins, and that these pure paraffins have clearly better characteristics, even compared to only slightly contaminated paraffins.

For this special application, the prices of the paraffins are higher than the prices of fatty alcohols. The required quantities of latent heat storage used directly correlate with the melting heat used, i.e. that substances which have a 20% higher melting heat, also accordingly have to be used in lesser quantities in order to achieve the same effect. For example, textiles can be produced with the same storage capacity with a lesser weight, and thus the wearing comfort can be clearly increased.

A further dehydration product of linear fatty alcohols are dialkyl ethers. These are likewise very non-polar and are characterized by sharp melting peaks and a high melting heat. In particular didodecyl ether and ditetradecyl ether have similar melting temperatures like e.g. $C_{18}$ or $C_{22}$ paraffins, respectively. Suitable catalysts for the dehydration to dialkyl ethers are clays, including boehmitic clays.

In the comparison of products produced by means of dehydrating fatty alcohol, dialkyl ethers and olefins/paraffins, the dialkyl ethers have the advantage that they can be produced economically, since for every 2 mol of fatty alcohol, only 1 mol of water has to be eliminated. As far as desired, the ethers may be stabilized against peroxide formation by means of antioxidants, wherein it is assumed, that in the micro- or macro-capsules, in which PCMs are frequently used, a decomposition of the ethers is sufficiently minimized by the capsule layer (frequently a polymer layer).

The latent heat storage material is preferably encapsulated by a polymer material as the capsule wall in micro-capsules with average particle sizes in the range from 1 to 200 μm, or in macro-capsules with average particle sizes in the range of more than 200 μm to 2 cm. Suitable polymer materials are, e.g., styrene divinylbenzene polymers or unsaturated polyesters. Preferred wall materials, since they are very resistant to ageing, particularly are thermoset polymers. Suitable thermoset polymer materials are, for example, cross-linked formaldehyde resins, cross-linked polyureas and cross-linked polyurethanes as well as cross-linked methacrylic acid ester polymers.

Melting temperature and melting heat are determined by means of DSC analytics. With a defined heating and cooling rate, the onset temperature (melting temperature) and the area below the curve (melting heat) are determined. The melting temperatures and heats of the paraffins and paraffin mixtures determined by means of DSC are respectively represented in the experiment part.

Figure 2:
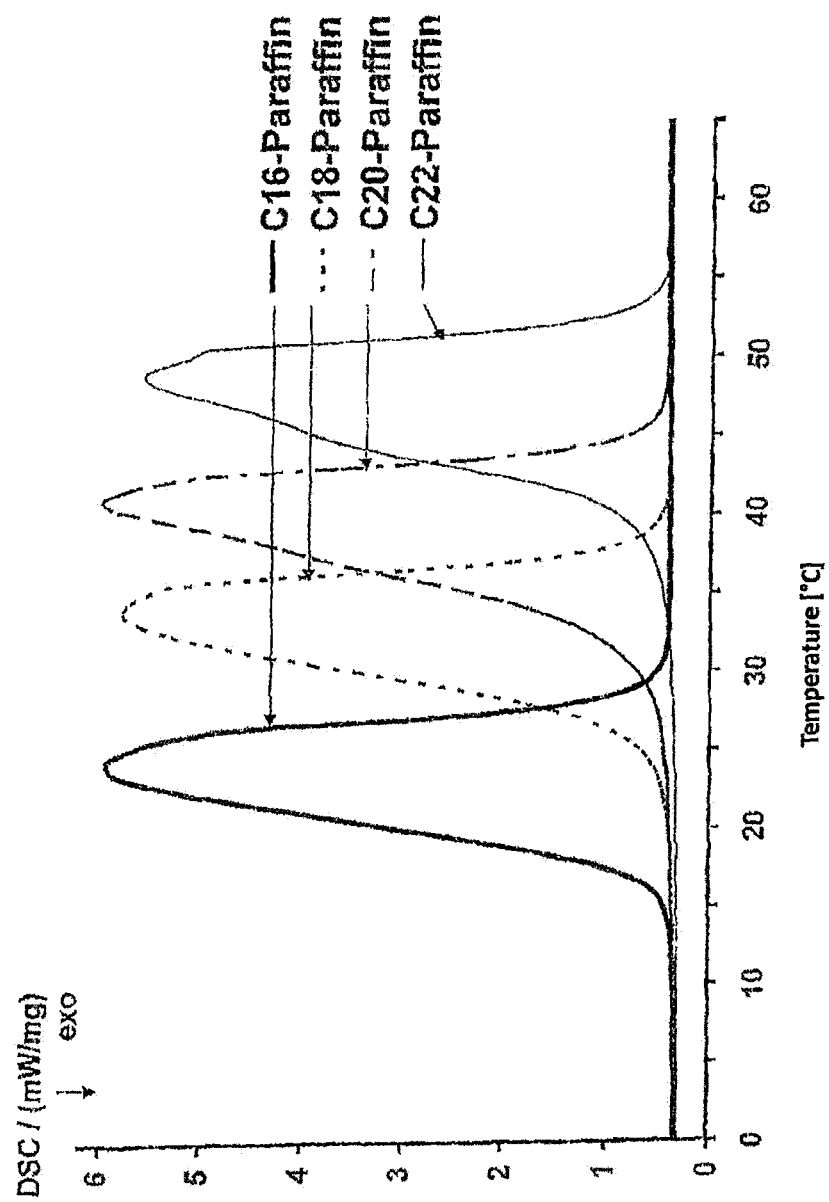
Figure 3:
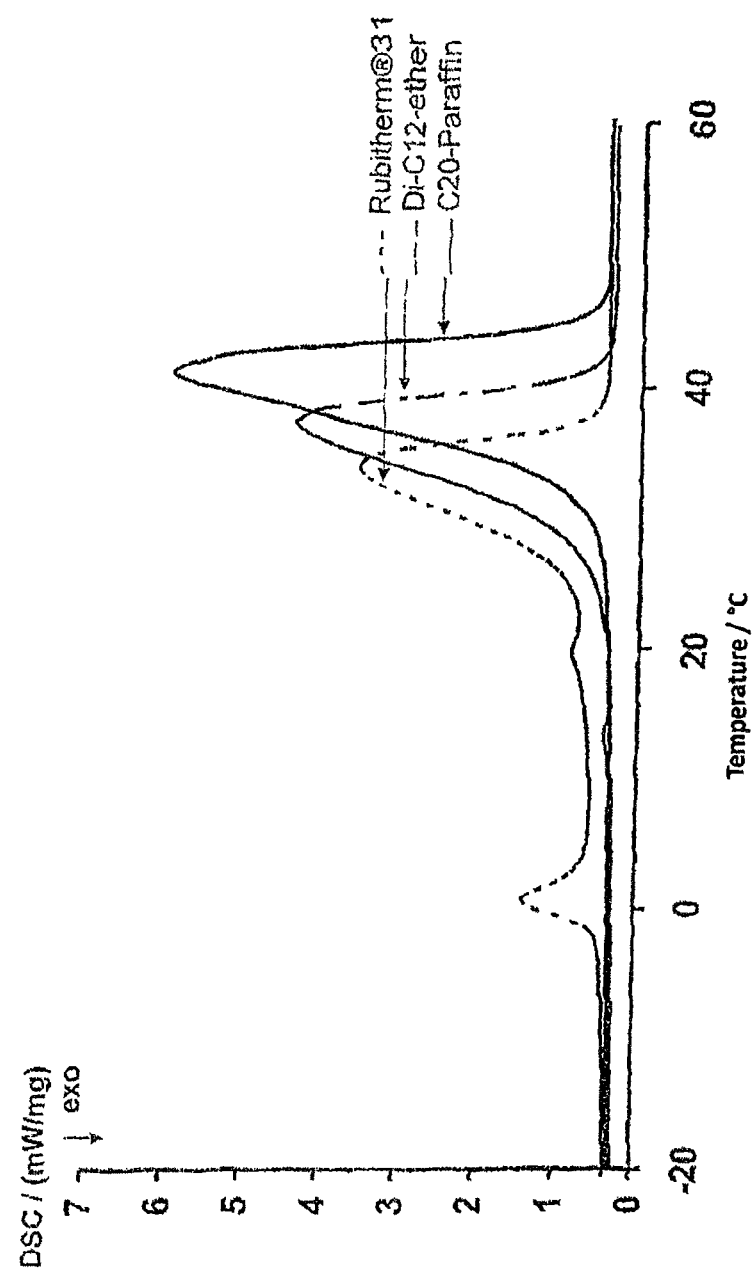
Figure 4:
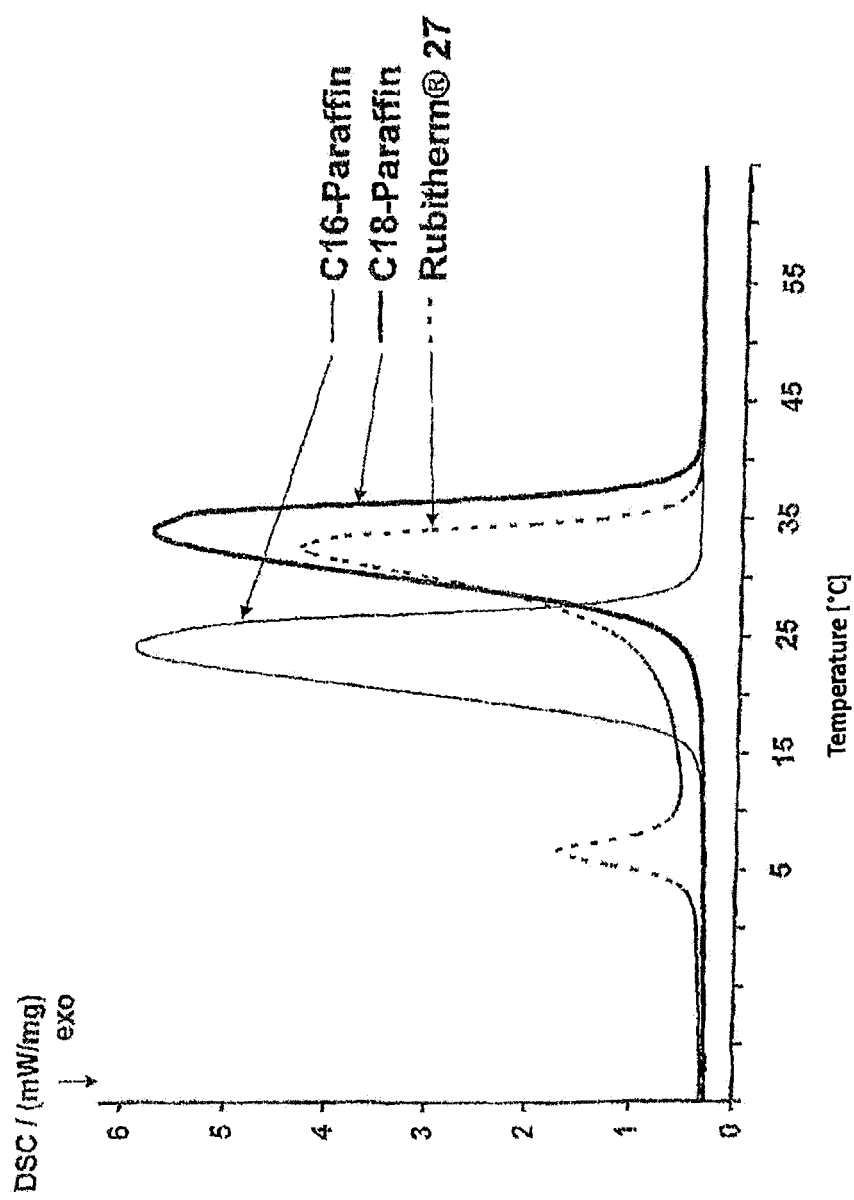
Figure 5:
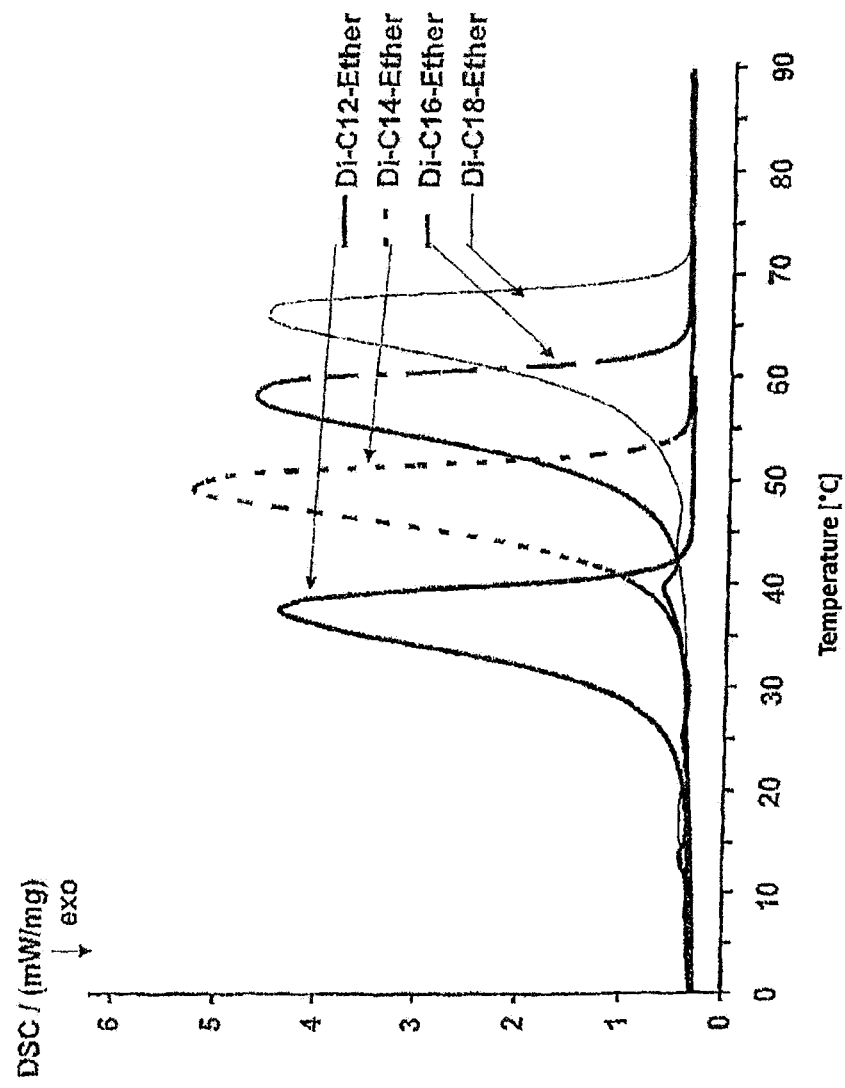

The figures show:

FIG. 1 C-chain distribution of paraffins Rubitherm® 27 and Rubitherm® 31;

FIG. 2 DSC diagram of C16 to C22 paraffins (pure);

FIG. 3 DSC diagram for comparison of Rubitherm® 31/Di-C12 ether/C20 paraffin;

FIG. 4 DSC diagram for comparison of Rubitherm® 27/C18 paraffin/C16 paraffin;

FIG. 5 DSC diagram Di-C12/C14/C16/C18 ethers, and

Figure 6:
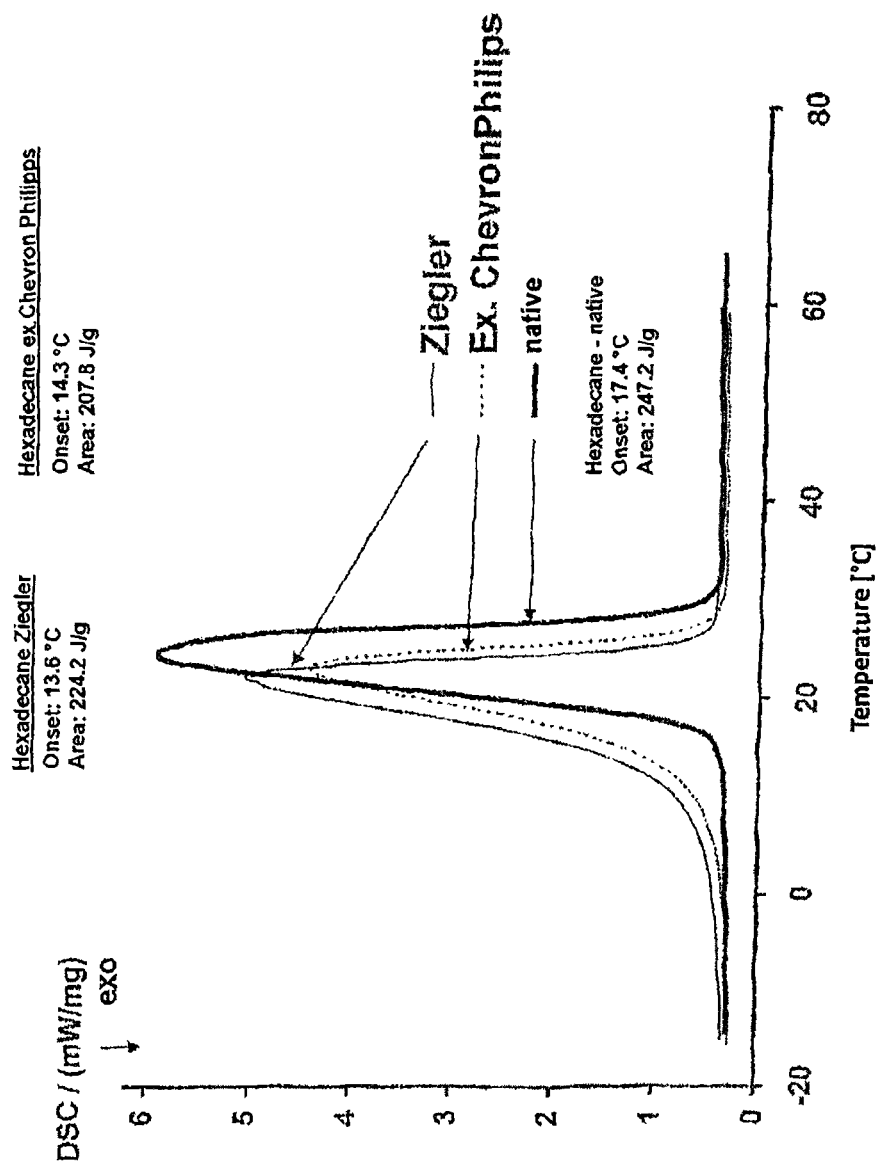

FIG. 6 DSC diagram for comparison of hexadecane from a synthetic/native source.

EXPERIMENT PART

The evaluation of the DSC analyses for the determination of melting enthalpy [J/g] and onset temperature was performed according to DIN 53765. All DSC curves were measured with the device DSC 204 F1 of the company Netzsch with heating and cooling rates of 10 K/min.

Comparative Example

Commercially available PCMB are Rubitherm® 27 and Rubitherm@ 31: Rubitherm® 27 and Rubitherm® 31 have the composition as apparent from FIG. 1 (determined via GC) and furthermore show the following characteristic determined via DSC:

TABLE 1

| Paraffin | Rubitherm ® 27 | Rubitherm ® 31 |
| --- | --- | --- |
| n-paraffin content [%] | 98.0 | 95.6 |
| Onset 1 [° C.] | 4 | −2 |
| Onset 2 [° C.] | 26 | 27 |
| Melting heat 1 [J/g] | 22.0 | 17.9 |
| Melting heat 2 [J/g] | 156.3 | 147.8 |

As an example for dehydrating linear fatty alcohols, the dehydration of hexadecanol to linear olefins (Experiment 1) and the hydrogenation of hexadecene (Experiment 2) are described in the following.

Experiment 1: Dehydrating Fatty Alcohols to Linear Olefins 2474 g of NACOL® 16-99 (purity 99.5%, based on renewable raw materials) were mixed with 500 g of $Al_2O_3$ and 60 ml of xylene in a 6 l flask and heated at up to 295° C., at the water separator for 4.5 hours. In that, 180 ml of water were formed. The hexadecene formed was distilled in vacuum. The yield was a mixture of alpha- and internal olefins.

Experiment 2: Hydrogenation of Linear Olefins to Linear Paraffins 685 g of the hexadecene obtained in Experiment 1 were hydrogenated for 7 hours at 98 according to a known method over a heterogeneous Ni-containing catalyst at 20 bar $H_2$ pressure and filtrated after cooling.

Fatty alcohols with chain lengths of $C_{16}$ to $C_{22}$ were used according to Experiments 1 and 2, and the following paraffins were obtained:

TABLE 2

| Paraffin | Hexadecane | Octadecane | Eicosane | Docosane |
| --- | --- | --- | --- | --- |
| n-paraffin (main component) [%] | 99.6 | 98.8 | 93.2 | 97.4 |
| n-paraffin (total) [%] | 99.8 | 98.9 | 96.8 | 98.6 |

TABLE 2-continued

| Paraffin | Hexadecane | Octadecane | Eicosane | Docosane |
|---|---|---|---|---|
| iso-paraffin [%] | 0.2 | 0.1 | 1.8 | 1.2 |
| Onset [° C.] | 17.4 | 27.4 | 32.5 | 40.6 |
| Melting heat [J/g] | 245.6 | 250.7 | 247.2 | 270.5 |

Experiment 3

Experiments 1 and 2 were repeated, however, a synthetic fatty alcohol (hexadecanol) from the Ziegler process with a purity of 95.6% was used as the alcohol.

Experiment 4

Experiment 2 was repeated, however, a synthetic olefin (hexadecene ex Chevron Phillips) with a purity of 94.2% was used as the olefin.

A comparison of the onset temperatures and melting heats for paraffins of different purity due to different production methods are compiled in the following table for hexadecane by way of example.

TABLE 3

| Paraffin | Hexadecane | Hexadecane | Hexadecane |
|---|---|---|---|
| Test number | 1 | 2 | 3 |
| Source | Native alcohol | Synth. alcohol | Synth. olefin |
| n-$C_{16}$ paraffin [%] | 99.6 | 91.8 | 92.3 |
| n-paraffin (total) [%] | 99.8 | 93.1 | 93.2 |
| iso-paraffin (total) [%] | 0.2 | 6.3 | 6.2 |
| Onset [° C.] | 17.4 | 13.6 | 14.3 |
| Melting heat [J/g] | 245.6 | 224.2 | 207.8 |

Experiment 5-7

Octadecane and Docosane were mixed at weight ratios of 1:1, 2:1, and 3:1, and the DSC curves were measured again.

TABLE 4

| Paraffin mixture [weight ratio] | $C_{18}/C_{22}$ paraffin 1:1 | $C_{18}/C_{22}$ paraffin 2:1 | $C_{18}/C_{22}$ paraffin 3:1 |
|---|---|---|---|
| Onset 1 [° C.] | −1.6 | −1.2 | −0.5 |
| Onset 2 [° C.] | 28.5 | 26.6 | 26.7 |
| Melting heat 1 [J/g] | 17.67 | 21.64 | 19.93 |
| Melting heat 2 [J/g] | 123.9 | 128.7 | 123.4 |

As an example for the partial dehydration of linear fatty alcohols, the dehydration of dodecanol to linear dialkyl ethers is described in the following.

Experiment 8-11: Dehydrating Linear Fatty Alcohols to Dialkyl Ethers 10 kg/h of NACOL® 12-99 (purity 99.2%, based on renewable raw materials) were led over $Al_2O_3$ beads in a fixed bed reactor (Ø=60 mm, l=900 mm) at 260° C. according to a known method. The didodecyl ether formed was subsequently distilled in vacuum.

TABLE 5

| Dialkyl ether | Didodecyl ether | Ditetradecyl ether | Dihexadecyl ether | Dioctadecyl ether |
|---|---|---|---|---|
| Purity [%] | 93.4 | 95.2 | 94.8 | 91.2 |
| Onset [° C.] | 30.4 | 41.8 | 51.5 | 59.3 |
| Melting heat [J/g] | 209.4 | 227.4 | 231.2 | 207.9 |

The invention claimed is:

1. A method for the production of a latent heat storage material, comprising:
   purifying fatty alcohols by distillation in order to obtain by distillation linear fatty alcohols comprising
      fatty alcohols that are more than 95% by mass linear,
      fatty alcohols that have more than 95% by mass even numbered chain lengths, and
      fatty alcohols that have a certain C-number at more than 95% by mass,
   followed by dehydrating of the linear fatty alcohols to obtain olefins and subsequently hydrogenating the olefins to obtain paraffins,
   wherein the paraffins are the latent heat storage material absorbing heat when liquefying and emitting stored heat when solidifying.

2. The method according to claim 1, characterized in that said paraffins comprise even-numbered chain lengths at more than 95% by mass.

3. The method according to claim 1, characterized in that said paraffins comprise a certain C-number at more than 97% by mass.

4. The method according to claim 1, characterized in that the fatty alcohols are cetyl alcohol or stearyl alcohol.

5. The method according to claim 1, characterized in that said fatty alcohols were obtained from naturally occurring vegetable raw materials.

6. The method according to claim 1, characterized in that said fatty alcohols are produced by ethylene oligomerization according to the Ziegler synthesis.

7. The method according to claim 1, characterized in that the latent heat storage material is encapsulated by a polymer material as the capsule wall material into microcapsules with average particle sizes in the range from 1 to 200 µm, or into macro-capsules with average particle sizes in the range from more than 200 µm to 2 cm.

8. The method according to claim 1, characterized in that the paraffin is hexadecane, octadecane, eicosan, or docosan.

9. The method according to claim 1, characterized in that the fatty alcohols are linear at more than 98% by mass.

10. The method according to claim 5, characterized in that the paraffin is hexadecane, octadecane, eicosan, or docosan.

11. The method according to claim 1, wherein the melting heat of the paraffins as latent heat storage material is at least 245.6 J/g.

12. A method for the production of a latent heat storage material, comprising:
   Purifying fatty alcohols, obtained from naturally occurring vegetable raw materials, by distillation in order to obtain by distillation linear fatty alcohols comprising
      fatty alcohols that are more than 95% by mass linear,
      fatty alcohols that have more than 95% by mass even numbered chain lengths, and
      fatty alcohols that have a certain C-number a more than 95% by mass,
   followed by dehydrating of the linear fatty alcohols to obtain olefins and subsequently hydrogenating the olefins to obtain paraffins, wherein the paraffin is hexadecane, octadecane, eicosan, or docosan, and wherein the paraffins are the latent heath storage material absorbing heat when liquefying and emitting stored heat when solidifying.

13. The method according to claim 12, characterized in that the fatty alcohols are linear at more than 98% by mass.

14. A method for absorbing and storing heat comprising producing a latent heat storage material, comprising:

purifying fatty alcohols by distillation in order to obtain by distillation linear fatty alcohols comprising fatty alcohols that are more than 95% by mass linear, fatty alcohols that have more than 95% by mass even numbered chain lengths, and fatty alcohols that have a certain C-number a more than 95% by mass, followed by dehydrating of the linear fatty alcohols to obtain olefins, subsequently hydrogenating the olefins to obtain paraffins, wherein the paraffins are the latent heath storage material; and absorbing heat when liquefying the latent heat storage material and emitting stored heat when solidifying the latent heat storage material.

* * * * *